US008771647B2

(12) United States Patent
Hachiya et al.

(10) Patent No.: US 8,771,647 B2
(45) Date of Patent: Jul. 8, 2014

(54) HUMAN PHOTOAGED SKIN MODEL

(75) Inventors: Akira Hachiya, Cincinnati, OH (US);
Tsutomu Fujimura, Tochigi (JP)

(73) Assignee: Kao Corporation, Tokyo (JP)

(*) Notice: Subject to any disclaimer, the term of this patent is extended or adjusted under 35 U.S.C. 154(b) by 748 days.

(21) Appl. No.: 11/766,522

(22) Filed: Jun. 21, 2007

(65) Prior Publication Data
US 2008/0010695 A1 Jan. 10, 2008

Related U.S. Application Data

(63) Continuation-in-part of application No. 11/311,239, filed on Dec. 20, 2005, now Pat. No. 7,642,402.

(51) Int. Cl.
*A01K 67/027* (2006.01)
(52) U.S. Cl.
CPC ....... *A01K 67/0271* (2013.01); *A01K 2267/035* (2013.01); *A01K 2227/105* (2013.01)
USPC ............................ 424/9.8; 435/371; 435/366
(58) Field of Classification Search
CPC ........... A61N 5/0616; A01K 2227/105; A01K 2267/0331; A01K 67/0271; A01K 2267/03; A61Q 19/00
See application file for complete search history.

(56) References Cited

U.S. PATENT DOCUMENTS

| | | | | |
|---|---|---|---|---|
| 5,709,816 A | * | 1/1998 | Yamaguchi et al. | 252/188.28 |
| 5,837,224 A | * | 11/1998 | Voorhees et al. | 424/59 |
| 2005/0283211 A1 | * | 12/2005 | McDaniel | 607/86 |

OTHER PUBLICATIONS

Berking et al. Photocarcinogenesis in human adult skin grafts, Carcinogenesis, 23(1): 181-7, 2002.*
Inokuchi et al. Effects of fibroblasts of different origin on long term maintenance of xenotransplanted human epidermal keratinocytes in immunodeficient mice, Cell Tissue Res. 281(2): 223-9, 1995.*
Hara et al, Construction of ectopic xenogeneic bone marrow structure associated with persistent multi-lineage mixed chimerism by engraftment of rat bone marrow plugs into mouse kidney capsules. Xenotransplantation, 10(3):259-66, 2003.*
Sano et al., The formation of wrinkles caused by transition of keratin intermediate filaments after repetitive UVB exposure, Arch Dermatol Res. 296(8):359-65, 2005.*
Naganumaa, et al., Delayed induction of pigmented spots on UVB-irradiated hairless mice. J Dermatol Sci. 25(1): 29-35, 2001.
Rieben, et al., Xenograft rejection: IgG1, complement and NK cells team up to activate and destroy the endothelium. Trends Immunol. 26(1): 2-5, 2005.
Jhappan, et al., Ultraviolet radiation and cutaneous malignant melanoma. Oncogene 22(20): 3099-112, 2003.
Del Bino, et al., Ultraviolet B induces hyperproliferation and modification of epidermal differentiation in normal human skin grafted on to nude mice. Br J Dermatol. 150(f): 658-67, 2004.
Haratake, et al., UVB-induced alterations in permeability barrier function: roles for epidermal hyperproliferation and thymocyte-mediated response. J Invest Dermatol. 108(5): 769-75, 1997.
S. Del Bino, et al., "Ultraviolet B induced hyperproliferation and and modification of epidermal differentiation in normal human skin grafted on to nude mice", British Journal of Dermatology, 2004: 150: 658-667.
Donald L. Bissett, et al., "An Animal Model of Solar-Aged Skin: Histological, Physical, and Visible Changes in UV-Irradiated Hairless Mouse Skin", Photochemistry and Photobiology vol. 46. No. 3. pp. 367-378. 1987.
Shuhei Imayama, et al., "Ultraviolet-B irradiation deforms the configuration of elastic fibers during the induction of actinic elastosis in rats", Journal of Dermatological Science 7 (1994) 32-38.
D. Nelson, et al., "Effects of UV Irradiation on a Living Skin Equivalent", Photochemistry and Photobiology, vol. 57. No. 5. pp. 830-837, 1993.

* cited by examiner

*Primary Examiner* — Deborah Crouch
*Assistant Examiner* — Titilayo Moloye
(74) *Attorney, Agent, or Firm* — Oblon, Spivak, McClelland, Maier & Neustadt, L.L.P.

(57) ABSTRACT

The present invention provides a human photoaged skin model and an animal model, and a method of making the same, for evaluating cosmetics and similar products in terms of their anti-aging or rejuvenating effect.

26 Claims, 5 Drawing Sheets

SEQUENCE LISTING

<160> NUMBER OF SEQ ID NOS: 1

<210> SEQ ID NO 1
<211> LENGTH: 39
<212> TYPE: DNA
<213> ORGANISM: Artificial
<220> FEATURE:
<223> OTHER INFORMATION: Synthetic DNA

<400> SEQUENCE: 1
ggccagtgaa ttgtaatacg actcactata gggaggcgg                    39

HUMAN PHOTOAGED SKIN MODEL

CROSS-REFERENCE TO RELATED APPLICATIONS

The present application is a continuation-in-part of U.S. Ser. No. 11/311,239, filed on Dec. 20, 2005, the entire contents of which is incorporated herein by reference.

FIELD OF THE INVENTION

The present invention relates to a skin model having human photoaged skin (hereinafter referred to as a human photoaged skin model), an animal model, and a method of creating such a human photoaged skin model and such an animal model.

BACKGROUND OF THE INVENTION

As we grow older, our skin—the human skin—ages; elasticity is lost and wrinkles appear. As compared with skin areas protected from light, other skin areas that tend to be constantly exposed to sunlight, especially to ultraviolet irradiation (UV), i.e., the face, neck, and shoulders, produce significant wrinkles, sagging skin, age spots, and freckles as a result of chronic exposure to UV rays. UV rays also act to lower elasticity of the skin, increase darkening or yellowing of the skin, and reduce the moisture content of the keratinous layer. The skin aging phenomenon uniquely occurring in UV-exposed skin areas is called photoaging. In order to elucidate the photoaging mechanism of the skin and to evaluate cosmetics, pharmaceuticals, and similar products which are thought to be useful for preventing or mitigating unfavorable outcomes of photoaging; i.e., wrinkles, age spots, and freckles, a photoaged skin model would be useful if it reflects conditions of the human photoaged skin more faithfully.

For creating a photoaged skin model or an animal model, chronic exposure to UV-rays has usually been performed. Hitherto, the following exemplary methods have been known: a method in which the back skin of a hairless mouse or the paw pad skin of a rat is continuously irradiated with UV rays every day for several weeks ((1) Bissett D L, Hannon D P, and Orr T V, Photochem Photobiol. 1987; 46(3): 367-78, (2) Imayama S., Nakamura K., Takeuchi M., Hori Y., Takema Y., Sakaino Y., and Imokawa G., J. Dermatol Sci. 1994 7(1): 32-8)) and a method in which a three-dimensional model skin is irradiated in vitro with a single dose of UV light ((3) Nelson D., Gay R J, Photochem Photobiol. 1993; 57(5): 830-7).

In relation to a model established on the basis of the human skin, there has been known a method in which a nude mouse to which human skin is transplanted is irradiated with a single dose of UV light ((4) Del Bino S., Vioux C., Rossio-Pasquier P., Jomard A., Demarchez M., Asselineau D., and Bernerd F., Br J. Dermatol. 2004; 150(4): 658-67). However, in this model system, daily, continuous irradiation for several weeks is not envisaged. Accordingly, although this prior art method makes use of human-derived skin, a sufficient photoaging condition cannot be induced in the transplanted human skin, because UV irradiation is performed for only a short period of time. Thus, the model requires improvements before being recognized as a satisfactory human photoaged skin model. Presently, there has never been obtained a satisfactory human skin model or an animal model that better mimics human photoaged skin.

SUMMARY OF THE INVENTION

The present invention is directed to a method of producing a human photoaged skin model, characterized in that a transplanted skin area of an immunodeficient non-human animal which has undergone transplantation of human skin is irradiated with UV-B light of 40-100 $mJ/cm^2$ for six or more consecutive weeks. This amount of UV, 40-100 $mJ/cm^2$ corresponds generally to the amount (1 MED) that causes a slight erythema on the grafted skin.

The present invention is also directed to a human photoaged skin model produced by the above-described method.

The present invention is also directed to an animal model which bears human photoaged skin and which is produced by the above-described method.

The above objects highlight certain aspects of the invention. Additional objects, aspects and embodiments of the invention are found in the following detailed description of the invention.

BRIEF DESCRIPTION OF THE DRAWINGS

A more complete appreciation of the invention and many of the attendant advantages thereof will be readily obtained as the same becomes better understood by reference to the following Figures in conjunction with the detailed description below.

DETAILED DESCRIPTION OF THE INVENTION

Figure 1:
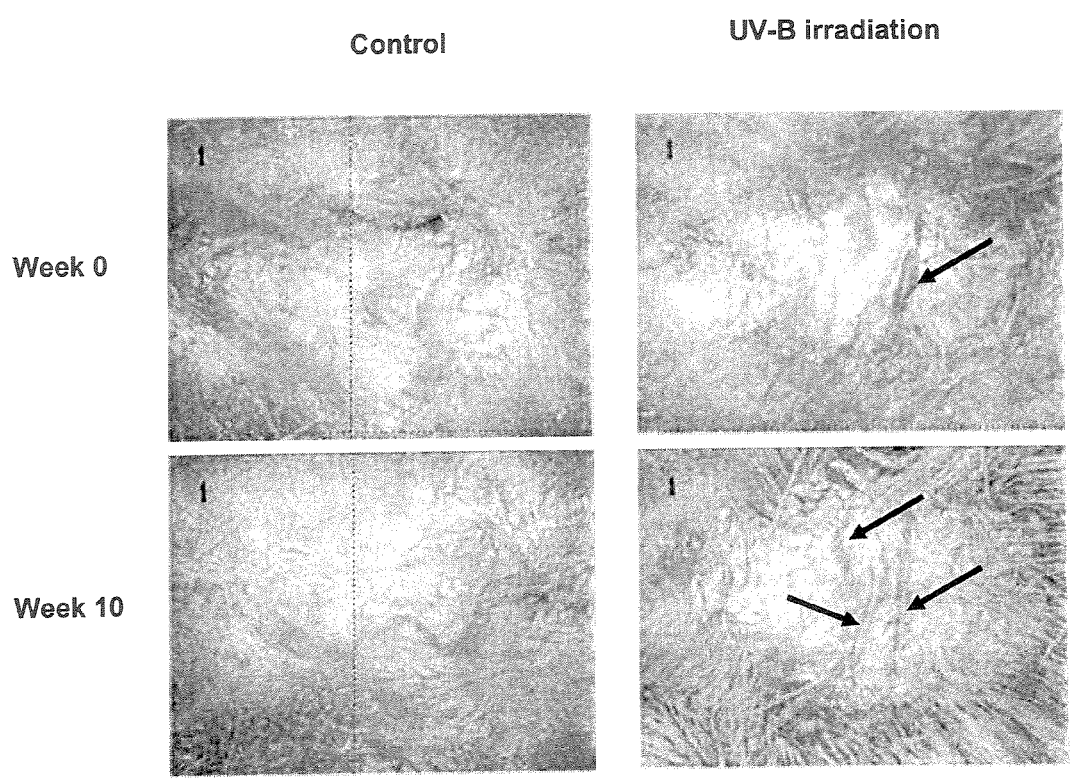
FIG. 1 shows comparison in terms of appearance of a transplanted skin area which had undergone 6-week irradiation with UV-B and was subsequently left for 4 weeks (i.e., at a point in time of 10 weeks) based on Example 1.

Unless specifically defined, all technical and scientific terms used herein have the same meaning as commonly understood by a skilled artisan in enzymology, biochemistry, cellular biology, molecular biology, cosmetics, and the medical sciences (e.g., dermatology, etc.).

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The present invention concerns provision of a skin model representing human photoaged skin (which may be referred to as a human photoaged skin model), an animal modeling human photoaging (which may be referred to as a human photoaging animal model), and a method for producing such a skin model and such an animal model. The skin model and the animal model according to the present invention are useful for evaluating the anti-aging and rejuvenating effect of cosmetics and quasi-drugs, among other products.

Through research of aging of the skin in animals to which human skin had been transplanted, the present inventors have found that when the transplanted skin area is irradiated with UV-B light of a specific dose for 4 to 8 weeks and then left as is for at least 3 weeks, there can be created an animal model bearing human "photoaged skin" which closely mimics actual human photoaging (see U.S. Ser. No. 11/311,239) when a foreskin is used as the transplanted skin.

Herein, the present inventors provide a method wherein ultraviolet irradiation (UV-B light) for six or more consecutive weeks to a transplanted skin area of an immunodeficient non-human animal resulted in the occurrence of wrinkles without allowing the skin to stand for 3 or more weeks (i.e., subsequent prolonged resting is unnecessary in the present invention) when a foreskin is used as the transplanted skin.

Much like the method disclosed in U.S. Ser. No. 11/311, 239, the method of the present invention enables, without taking a long time, provision of a human photoaged skin model or an animal model exhibiting aged skin conditions consistently, and use of such a model enables more precise elucidation of the mechanism of human skin aging and more accurate evaluation of anti-aging/rejuvenating substances.

According to the present invention, the human photoaged skin model is produced as follows: a transplanted skin area of an immunodeficient non-human animal which has undergone transplantation of human skin is irradiated with UV-B light of 40-100 $mJ/cm^2$ (approximately 1 MED) for six or more consecutive weeks.

As used herein, the expression "human photoaged skin model" means a certain area of skin in an animal model of human photoaged skin, the animal model bearing human photoaged skin showing the effect of aging similar to that caused by natural aging (e.g., wrinkles, saggy skin, age spots, freckles, lowered skin elasticity, increase in darkening or yellowing of the skin, and reduced water content of the keratinous layer).

In the method of the present invention, an immunodeficient animal is used as the animal. Examples of the animal include immunodeficient mice such as SCID mice, BALB cA-nu/scid or B-17/Icr-Scid, and athymic nude mice; and immunodeficient rats such as F344 Jc1-rnu. From the viewpoint of tolerance to long-term UV irradiation, use of immunodeficient mice is preferred.

These animals are preferably placed under SPF conditions, one animal per cage. The animals are commercially available from Clea Japan, Inc. or Taconic (NY).

A patch of human skin is transplanted to the above-mentioned immunodeficient non-human animal, and the patch is preferably a portion of the skin which is protected from light; e.g., the foreskin of a newborn baby or, if obtained from an adult, abdominal skin. Such a skin patch is available from circumcision or plastic surgery, or from a cadaveric skin supplied by the Skin Center.

The patch of human skin is aseptically collected so as to have a thickness of 2 to 5 mm. Until grafting to an animal, the skin patch is preferably preserved in a suitable culture medium, such as DMEM supplemented with L-glutamine and an antibiotic/antimycotic (Invitrogen, CA), under sparse conditions while the temperature is maintained at 2-4° C.

Skin transplantation to an animal may be carried out in accordance with a method known in the art (Demarchez M., Hartmann D J, Herbage D., and Ville G., Dev Biol. 1987; 121(1): 119-29). For example, the following method may be used.

Under anesthesia with isofluorane/oxygen or Nembutal, a 2×2 to 3×3 $cm^2$ wound incision is made in the dorsal skin of the animal. Before the incision was made, the skin is preferably shaved. Subsequently, a human skin graft having the same size is transplanted to the incision, and then sutured with a Nylon suture (10-20 stitches). Upon completion of suturing, analgesic treatment is preferably carried out by adding sensorcaine to the border between the skin graft and mouse skin.

Until the mice have recovered from anesthesia, they are kept in a 37° C. incubator.

Preferably, UV irradiation is started when the transplanted skin has been completely healed; i.e., about 10 weeks after transplantation.

The UV light employed is preferably UV-B light having a wavelength falling within a range of 290 to 320 nm. More preferably, the UV light has a peak in the vicinity of 302 nm.

Irradiation is preferably performed using a UV lamp held 5 to 80 cm, preferably 30 to 50 cm or thereabouts, away from the animal (specifically, the transplanted skin graft) in view of minimized uneven irradiation and ease of handling.

The UV dose is 40 to 100 $mJ/cm^2$ (approximately 1 MED). In a preferred embodiment, the UV dose ranges from 40 to 60 $mJ/cm^2$ in the case of abdominal skin, and ranges from 80 to 100 $mJ/cm^2$ in the case of foreskin. However, other ranges and subranges within the range of 40 to 100 $mJ/cm^2$ are clearly contemplated by the present invention. For example, the UV dose ranges may be from 60 to 100 $mJ/cm^2$ or 80 to 100 $mJ/cm^2$.

In the present invention, the irradiation is performed for six or more consecutive weeks. In one embodiment of the present invention, the irradiation ranges from 6 to 8 weeks. However, extended exposure periods are also embraced by the present invention, including: seven weeks, eight weeks, nine weeks, ten weeks, eleven weeks, twelve weeks, etc. and all sub-part thereof.

For avoiding any acute effect of UV rays, the following UV irradiation protocol is mentioned as an example, which is equally applicable to any of the ranges and sub-ranges embraced by the present invention including those recited above. In the exemplary protocol, during the first three weeks after commencement of irradiation, the dose is increased at a rate of 10 $mJ/cm^2$ a week, and after the third week, the dose is maintained at 60 $mJ/cm^2$ at abdominal skin, and at 100 $mJ/cm^2$ at foreskin. That is, a preferable regimen may be as follows: at abdominal skin, 40 $mJ/cm^2$ for the first week of UV irradiation, 50 $mJ/cm^2$ for the second week, and 60 $mJ/cm^2$ for the third and subsequent weeks. At the foreskin, 80 mJ/cm² for the first week of UV irradiation, 90 mJ/cm² for the second week, and 100 mJ/cm² for the third and subsequent weeks.

Preferably, UV irradiation is performed in such a manner that the above UV dose is irradiated once a day, 5 to 6 days per week. Alternatively, the UV irradiation can be five or six times a week spaced out at a predetermined interval. Further, the UV irradiation may be continual or pulsed during the exposure time.

In an embodiment of the present invention, the total UV-B dose is approximately 1.65 J/cm² at abdominal skin, and approximately 2.85 J/cm² at foreskin. In this context, the term "approximately" means that the total UV-B dose varies by up to 50%, preferably by up to 20%, more preferably by up to 10%, and most preferably by up to 5%.

Figure 4:
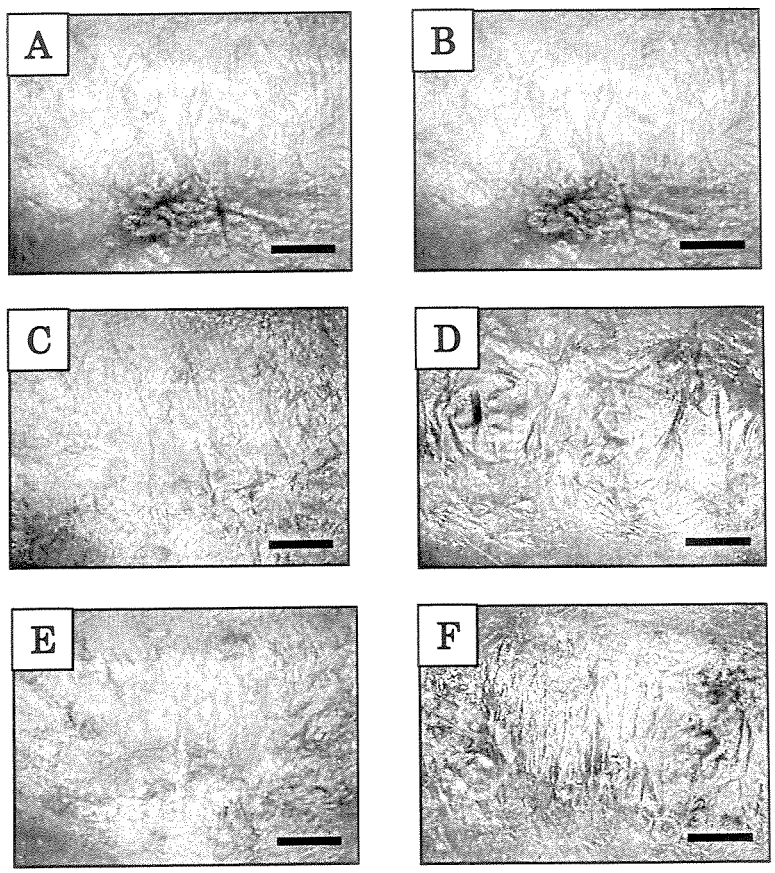
FIG. 4 shows the wrinkle aggravation on abdominal skin xenograft following UVB irradiation in Example 2. Human abdominal skin xenografts on SCID mice were exposed to 1-1.5 MED UVB 5 times weekly for 6 weeks. Changes in wrinkle aggravation were monitored using a Charm View on a non-exposed control (A, C, and E) or a UVB-exposed (B, D and F) skin xenograft at 0 (A and B), 3 (C and D), and 6 (E and F) weeks. Bar=3 mm.

As shown in FIG. 4, the thus-developed aging skin conditions closely mimic photoaged skin in terms of formation of wrinkles, etc.

The thus-produced human photoaged skin model and animal model of the present invention are useful for the elucidation of the mechanism of human skin aging, evaluation of anti-aging and/or aging reversing substances, and regenerative medicine.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

Human Photoaged Skin Model with Resting

1. Skin Grafting

A skin graft was transplanted to each of immunodeficient mice (female, 4-6 week old). Throughout the experiment period, the mice were raised under pathogen-free conditions. Immediately before transplantation of the skin graft, the dorsal hair was removed with an electric shaver, and isofluorane/oxygen (3%/0.8 liter) was used for anesthesia. During the grafting surgery, anesthetic conditions were maintained by use of isofluorane/oxygen (2%/0.7 liter). The dorsal skin of each mouse was scraped, to thereby produce a wound bed having a diameter of about 2.0-3.0 cm. A supplied skin graft; i.e., prepuce from circumcision, a patch of skin from plastic surgery was grafted and sutured. The supplied patch of skin had been preserved in DMEM supplemented with L-glutamine and an antibiotic/antimycotic (Invitrogen, CA) until grafting (2-4° C.). After suturing, analgesic treatment was performed by adding sensorcaine to the boundary between the skin graft and mouse skin. Until recovery from the anesthetic, the mice were accommodated in a 37° C. incubator.

2. UV-B Irradiation

UV-B Irradiation was started after healing; i.e., at least 10 weeks after the transplantation surgery. A UV lamp which emits UV-B light having a peak in the vicinity of 302 nm wavelength was employed, and the distance between the lamp and the skin graft was about 30 cm.

Since MED (minimal erythema dose) of the transplanted skin was found to correspond to 50 to 80 mJ/cm² (in this experiment, the transplanted skin is mainly a foreskin), chronic irradiation of UV-B was decided to be started from a level of 80 mJ/cm². Irradiation was performed 5 days per week for 6 consecutive weeks. Before entering the third week, UV dose was increased by 10 mJ/cm² per week, and during the third to the sixth week, the dose of UV-B irradiation was maintained at 100 mJ/cm². During irradiation, the mice were allowed to freely move around in a transparent container having a floor area of 100 cm².

3. Evaluation of the Conditions of Aged Skin (1) After the start of irradiation, the surface of the transplanted skin graft was observed under a Charm View microscope (registered trademark; Moritex, Japan) using transmitted light that was reflected. In addition, digital images were captured every 2 weeks.

(2) By use of a replica agent, a replica of the transplanted skin was produced, and the replica was subjected to the following surface roughness analysis.

<Surface Roughness Analysis on Replica>

Replicas were prepared before the start of the test, and in the 2nd, 4th, and 10th weeks after the start of the test. During preparation of replicas, the animals were maintained under anesthesia with isofluorane/oxygen (2%/0.7 liter).

The skin replicas prepared by use of SILFLO (Flexico Developments) were each compressed to as flat as possible through use of another replica agent (GC exafine) with the application of pressure under a plate or similar means, and the resultant replicas were analyzed.

The three-dimensional configuration of each replica was measured by use of PRIMOS Compact (product of GF Messtechnik). After measurement, moiré fringes were eliminated through use of a filter.

A linear surface roughness analysis was performed as follows. On each of the obtained replicas, an analytical line (straight line) having a length of 7-9 mm was drawn. Along this line, linear roughness parameter values were obtained. This process was performed carefully so as not to include any shape, such as a wart, that is not considered to be caused by wrinkles. In a plane analysis, a rectangular area of about (4-5 mm)×(7-9 mm) was chosen in the central part of each of the above replicas, and within that area, the plane analysis was performed. In this case also, the area was appropriately selected so as not to include any irrelevant shape such as a wart.

The parameters employed for comparison are Ra (arithmetical mean roughness) and Rz (10-point mean roughness).

Ra: arithmetical mean roughness

Rz: 10-point mean roughness, which is a sum of the mean value of the first high to the fifth high height of monticules and the first deep to the fifth deep depth of valleys).

(3) Gene Expression Analysis with a Gene Chip

Grafted skin was harvested after 24 hours after the final irradiation. Total RNA was extracted with a Trizol reagent (Invitrogen, CA), and cleaned up using an RNeasy mini kit (Qiagen, CA). Purity of each RNA sample (28 s/18 s) was verified using an Aligent bioanalyzer. Biotin-labeled target cRNA was generated according to Affymetrix protocols. In short, double-stranded cDNA was generated using T7 (-dT) 24 primer 5'-GGCCAGTGAATTGTAATACGACTCACTAT AGGGAGGCGG-3' (sequence number 1) and Superscript II reverse transcriptase. cRNA from each sample was hybridized to Human Genome U133 plus 2.0 chip.

4. Results (1) Appearance

FIG. 1 shows the appearance of a grafted skin area as photographed after the relevant area was irradiated with UV-B for 6 weeks and subsequently left for 4 weeks (at a point of week 10) for comparison with a control. The grafted skin was foreskin. As is apparent from FIG. 1, the control skin did not show any significant change in skin surface configuration, whereas in the case where UV-B irradiation was performed, changes in shape including wrinkle-like linear changes, or an increase in such changes, were observed (see the arrows).

(2) Analysis of Replicas

Figure 2:
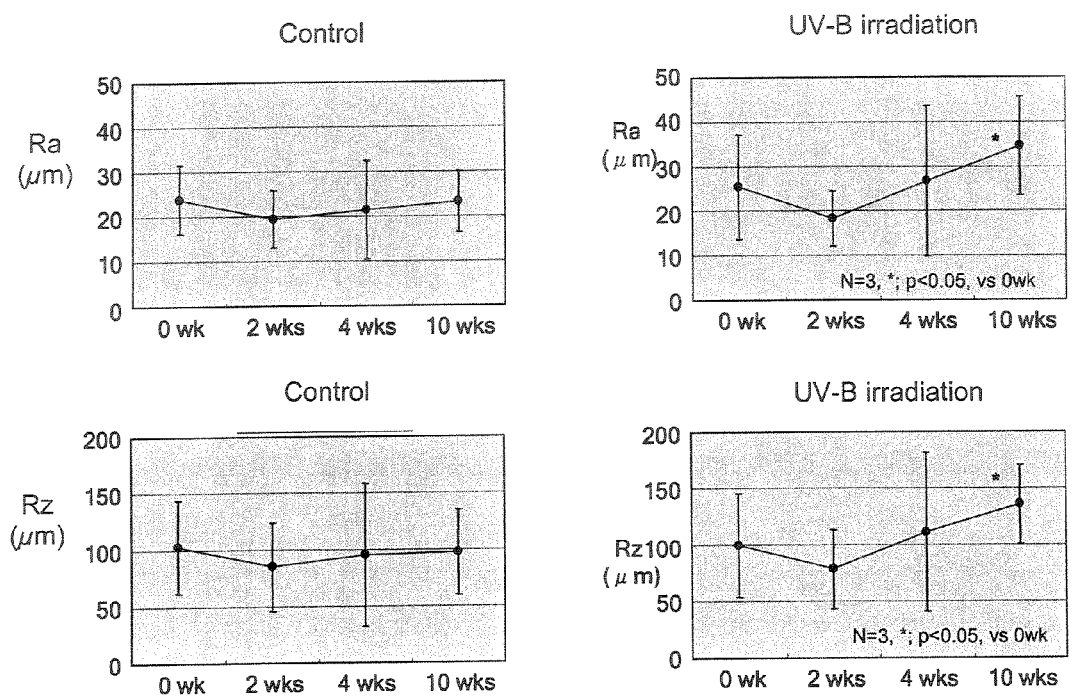
FIG. 2 depicts graphs from Example 1 showing the results of a three-dimensional surface roughness analysis performed on replicas of the skin areas which had undergone UV-B irradiation (plotted after irradiation for 2 and 4 weeks) and 6-week UV-B irradiation with subsequent resting for 4 weeks (i.e., at a point in time of 10 weeks).

FIG. 2 provides graphs showing, for comparison with a control, the results of a three-dimensional surface roughness analysis on replicas of grafted skin areas after the relevant areas were irradiated with UV-B, wherein the skin graft employed was foreskin and the analysis was performed 2 and 4 weeks after the start of UV-B irradiation and the analysis was also performed after 6-week UV-B irradiation with subsequent 4-week resting (i.e., at a point of week 10). As is apparent from FIG. 2, in the control case, skin showed almost no change for both roughness parameter Ra (arithmetical mean roughness) and Rz (10-point mean roughness); in other words, no change was observed in terms of roughness of the skin surface, whereas in the UV-B irradiation group, at the point in time of weeks (i.e., 6 weeks of UV-B irradiation and 4 weeks of standing as being left), statistically significant increases were observed for both Ra and Rz. This result coincides with the formation of uneven skin surface; i.e., the wrinkle-like lines as shown in FIG. 1.

Figure 3:
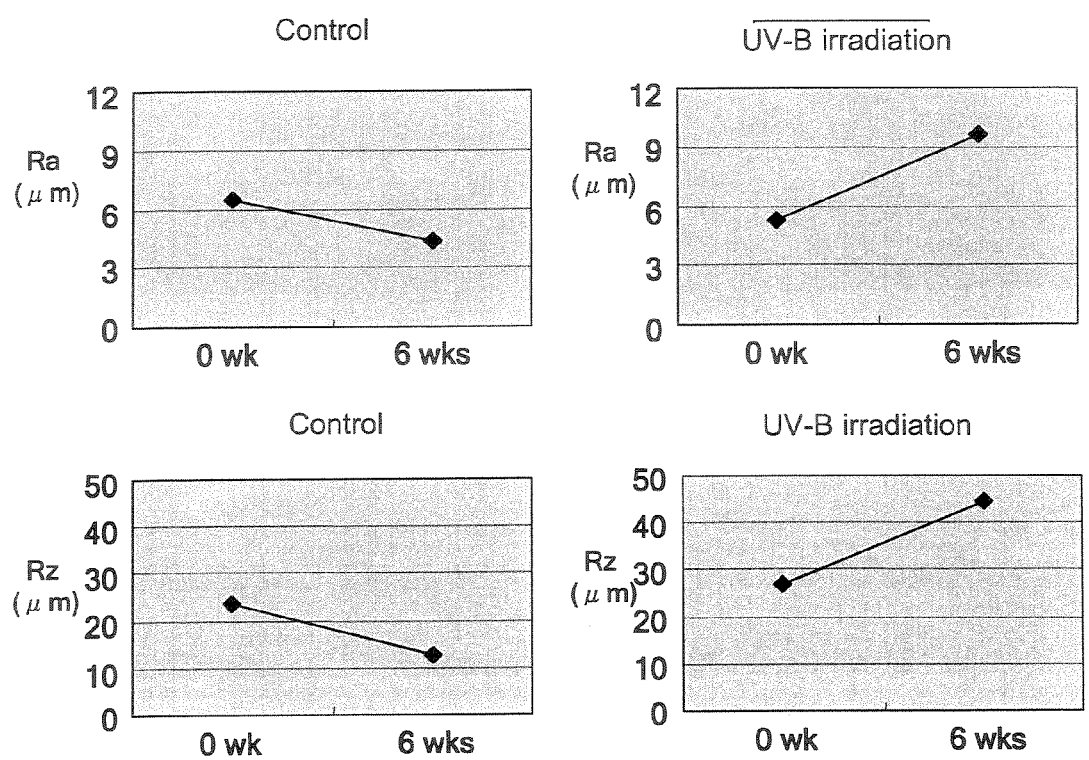
FIG. 3 depicts graphs from Example 1 showing the results of a three-dimensional surface roughness analysis performed on replicas of the skin areas which had undergone 6-week irradiation with UV-B light, in which abdomen-derived skin grafts were employed.

FIG. 3 provides graphs showing, for comparison with a control, the results of a three-dimensional surface roughness analysis on replicas of grafted skin areas after the relevant areas were irradiated with UV-B for 6 weeks, wherein the skin graft employed was abdomen-derived skin. As is apparent from FIG. 3, in the control case, skin showed almost no change for both roughness parameter Ra (arithmetical mean roughness) and Rz (10-point mean roughness); in other words, no change was observed in terms of roughness of the skin surface, whereas in the UV-B irradiation group, at the point in time of 6 weeks of irradiation, increases in both Ra and Rz were observed. This result coincides with the formation of uneven skin surface; i.e., the wrinkle-like lines as shown in FIG. 1.

(3) Gene Expression Profile

After confirmation of RNA quality, we generated the gene expression profile for UVB irradiation abdominal grafts for comparison with the non-irradiated control. The estimated changes of mRNA transcript concentration between the control and UVB groups were illustrated in log/log scatter plot. In grafted abdomen, over-expressed genes were keratin 6, keratin 16, keratin 12, MMP 13, MMP 1, involucrin, and filaggrin, and under-expressed genes were collagen I, collagen III, collagen IV, collagen VI, and MMP2.

Example 2

Human Photoaged Skin Model without Resting

1. Grafting Abdominal Skin onto SCID Mice

Animals were handled according to the guidelines of Institutional Animal Care and Use Committee at Cincinnati Children's Hospital. Female Icr-Scid mice 4-6 weeks old (Taconic, N.Y.) were kept under pathogen-free condition throughout the experiments and maintained on a standard laboratory diet and water ad libitum. After one week of acclimation, animals were shaved with an electric clipper to remove the dorsal hair. Mice were anesthetized by isofluorane/oxygen (3%/0.8 liter), and maintained using isofluorane/oxygen (2%/0.7 liter) throughout the surgery. The shaved dorsal skin was treated with a non-staining surgical scrub upon confirmation of anesthesia. The dorsal site was cut to produce a wound bed of approximately 2.0-3.0 cm in diameter.

Full-thickness abdominal skin from abdominoplasty (University Hospital, Cincinnati, Ohio) was sutured in place with a reverse cutting precision monofilament PS-3, 6-0. The edges of the graft bed were treated with sensorcaine to provide analgesia. Following the surgery, the mice were kept in an incubator at 37° C. either for an hour or until recovered from anesthesia. The grafted skin was observed using a Charm View fitted with or without a polarizing lens (Moritex Corporation, Tokyo, Japan).

2. UVB Irradiation

UVB irradiation of the human skin xenograft on the SCID mice was performed approximately 8 weeks after the grafting when healing was complete. UVB irradiation was performed as described by Takema et al except for the source of UVB (Takema et al, 1996). Briefly, a bank of two UVB lamps (34-0044-01 lamps, UVB, Upland, Calif.) with a filter yielding a peak of emission near 302 nm was used and the energy output was measured with a UV light meter, UV-340 MSR7000 (Lutron Electronic Enterprise Co., ltd, Taiwan). The distance from the filters to the surfaces of skin was approximately 30 cm. A progressive UVB exposure regimen was used starting at approximately 40 mJ/cm$^2$ which equals to 1 minimal erythema dose (MED) of grafted Caucasian abdominal skin, and was increased by 10 mJ/cm$^2$ per week until week 3. The irradiation dose of 60 mJ/cm$^2$ was kept constant for the remaining period of exposure. The grafted abdominal skin was irradiated 5 times weekly for 6 weeks yielding the total UVB dose of approximately 1.65 J/cm$^2$. During the period of exposure, mice with human skin xenografts could move around freely in the approximately 100 cm$^2$-clear container.

3. Image Analysis of Replica of Human Skin Xenografts after UVB Irradiation

A replica of the abdominal skin xenograft was produced by the use of a replica agent, SILFLO, (Flexico Developments, Potters Bar, UK). Skin replicas were prepared before irradiation, and in the 3$^{rd}$ and the 6$^{th}$ weeks after initial exposure. In brief, skin replicas were compressed as flat as possible using GC exafine (GC Corporation, Tokyo, Japan). The three-dimensional optical measurement of each replica was depicted using PRIMOS Compact (GF Messtechnik GmbH, Berlin, Germany). After measurement, moiré fringes were eliminated through use of a filter.

A linear surface roughness analysis was performed as follows. An analytical straight line (7-9×mm) was drawn on each replica. Along this line, linear roughness parameter values were assessed. This process was performed carefully to exclude any shape that is not wrinkle. In a plane analysis, a rectangular area (4-5 mm×7-9 mm) was chosen in the central part of each replica. Within that area, the plane analysis was performed, and 4 parameters, Ra and Sa (arithmetical mean roughness) and Rz and Sz (10-point mean roughness) were used as a degree of wrinkle indicator. Ra and Rz are one-dimensional and Sa and Sz are two-dimensional parameters.

Ra and Sa: arithmetical mean roughness

Figure 5:
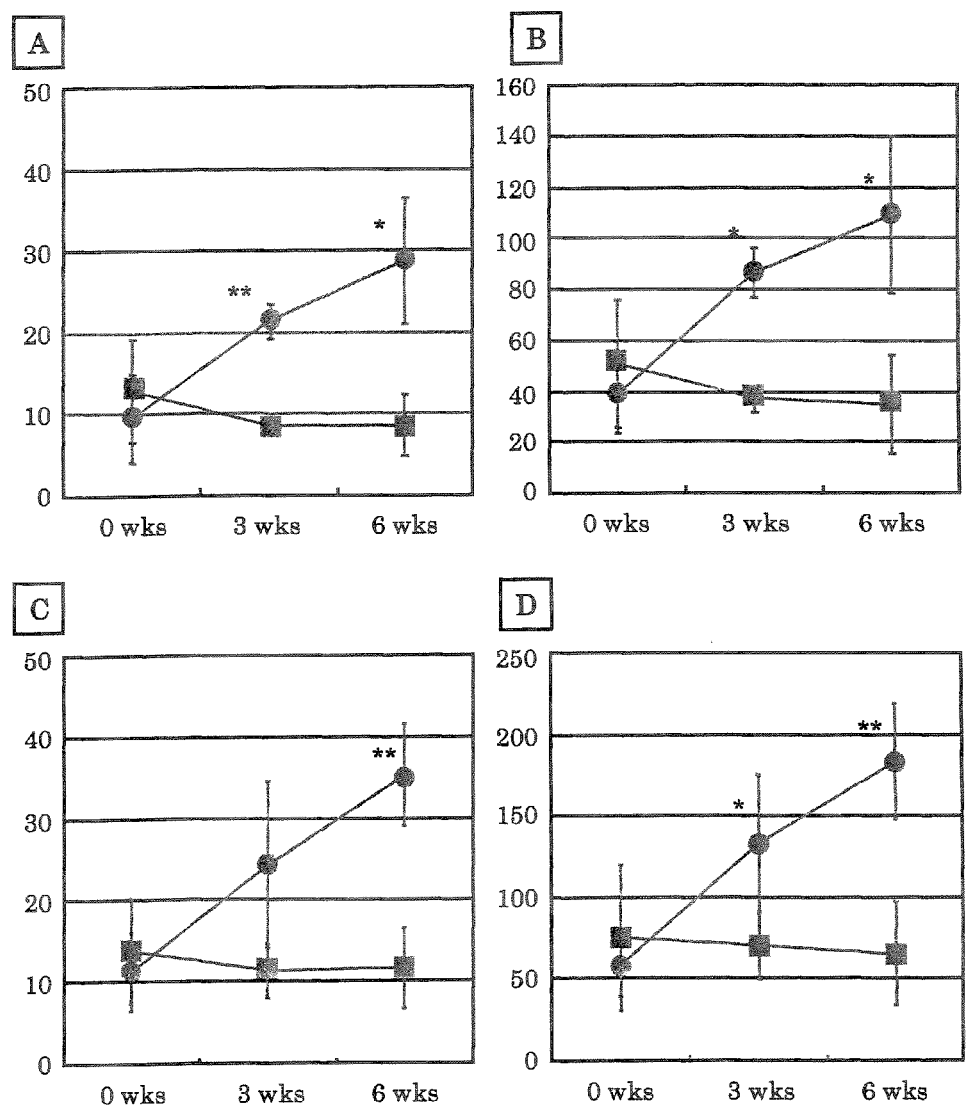
FIG. 5 depicts the image analysis of xenograft replicas and demonstrates significant UVB-induced wrinkle aggravation as in Example 2. The three-dimensional configuration was measured using PRIMOS Compact on each human skin xenograft replica prepared with the replica agent, SILFLO and compressed flat using the replica agent, GC exafine. The parameters employed for comparison were Ra and Sa (arithmetical mean roughness) and Rz and Sz (10-point mean roughness). Ra and Rz are one-dimensional and Sa and Sz are two-dimensional parameters. (A) Ra, (B) Rz, (C) Sa, and (D) Sz. The values of control are shown as gray squares and the data for UVB-irradiated skin xenografts are shown as gray circle. The values reported represent means±SD from 4-6 independent xenografts per group. * $p<0.05$, ** $p<0.01$ (compared to the values at 0 weeks).

Rz and Sz: 10-point mean roughness, which is a sum of the mean value of the first highest height to the fifth highest height of monticules and the first deepest depth to the fifth deepest depth of valleys 4. Results (1) Appearance FIG. 4 shows the appearance of a grafted skin area as photographed after the relevant area was irradiated with UV-B for 6 weeks. As is apparent from FIG. 4, the control skin did not show any significant change in skin surface configuration, whereas in the case where UV-B irradiation was performed, changes in shape including wrinkle-like linear changes, or an increase in such changes, were observed, (2) Analysis of Replicas FIG. 5 provides graphs showing, for comparison with a control, the results of a three-dimensional surface roughness analysis on replicas of grafted skin areas after the relevant areas were irradiated with UV-B, wherein the skin graft employed was abdominal skin and the analysis was performed 3 and 6 weeks after the start of UV-B. As is apparent from FIG. 5, in the control case, skin showed almost no change for all roughness parameter Ra and Sa (arithmetical mean roughness) and Rz and Sz (10-point mean roughness); in other words, no change was observed in terms of roughness of the skin surface, whereas in the UV-B irradiation group, at the point in time of 3 weeks, statistically significant increases were observed for Ra, Rz and Sz, and at the point in time of 6 weeks, statistically significant increases were observed for all roughness parameters. This result coincides with the formation of uneven skin surface; i.e., the wrinkle-like lines as shown in FIG. 4.

Numerous modifications and variations on the present invention are possible in light of the above teachings. It is, therefore, to be understood that within the scope of the accompanying claims, the invention may be practiced otherwise than as specifically described herein.

the skin area is irradiated with 50 to 100 mJ/cm$^2$ of UV-B radiation during a second week of the period;

the skin area is irradiated with 60 to 100 mJ/cm$^2$ of UV-B radiation during a third week, a fourth week, a fifth week, and a sixth week of the period; and the skin area is optionally irradiated with 60 to 100 mJ/cm$^2$ of UV-B radiation during an optional seventh week and an optional eighth week of the period;

irradiating the skin area comprises irradiating with a total dose of UV-B radiation of from approximately 1.65 J/cm$^2$ to approximately 2.85 J/cm$^2$; and the skin area is in the condition suitable for use as a human photoaged skin model when the skin area has at least one condition selected from the group consisting of wrinkles, sagginess, age spots, freckles, lowered elasticity, increased darkening, increased yellowing, and reduced keratinous layer water content.

2. The method according to claim 1, wherein the immunodeficient mouse is a SCID mouse.

3. The method according to claim 2, wherein the SCID mouse is BALB cA-nu/SCID or B-17/Icr-SCID.

4. A method for producing a human photoaged skin model, comprising:

irradiating a skin area of an immunodeficient mouse; and discontinuing irradiation when the skin area is in a condition suitable for use as a human photoaged skin model; wherein:

the skin area comprises human skin transplanted to the immunodeficient mouse;

irradiating the skin area comprises irradiating for a period of from six to eight consecutive weeks, during which:

the skin area is irradiated with 80 to 90 mJ/cm$^2$ of UV-B radiation during a first week of the period;

the skin area is irradiated with 90 to 100 mJ/cm$^2$ of UV-B radiation during a second week of the period;

the skin area is irradiated with 100 mJ/cm$^2$ of UV-B radiation during a third week, a fourth week, a fifth week, and a sixth week of the period; and

The invention claimed is:

1. A method for producing a human photoaged skin model, comprising:

irradiating a skin area of an immunodeficient mouse; and discontinuing irradiation when the skin area is in a condition suitable for use as a human photoaged skin model; wherein:

the skin area comprises human skin transplanted to the immunodeficient mouse;

irradiating the skin area comprises irradiating for a period of from six to eight consecutive weeks, during which:

the skin area is irradiated with 40 to 50 mJ/cm$^2$ of UV-B radiation during a first week of the period;

the skin area is optionally irradiated with 100 mJ/cm$^2$ of UV-B radiation during an optional seventh week and an optional eighth week of the period;

irradiating the skin area comprises irradiating with a total dose of UV-B radiation of from approximately 1.65 J/cm$^2$ to approximately 2.85 J/cm$^2$; and the skin area is in the condition suitable for use as a human photoaged skin model when the skin area has at least one condition selected from the group consisting of wrinkles, sagginess, age spots, freckles, lowered elasticity, increased darkening, increased yellowing, and reduced keratinous layer water content.

5. The method according to claim 1, wherein irradiating the skin area comprises performing continuous irradiation.

6. The method according to claim 1, wherein irradiating the skin area comprises performing pulsed irradiation.

7. The method according to claim 1, wherein irradiating the skin area comprises irradiating five times per week.

8. The method according to claim 1, wherein the total dose of UV-B radiation is approximately 1.65 J/cm$^2$.

9. The method according to claim 1, wherein the total dose of UV-B radiation is approximately 2.85 J/cm$^2$.

10. An animal model which bears human photoaged skin and which is produced by the method according to claim 1.

11. The method according to claim 8, wherein the human skin is abdominal skin.

12. The method according to claim 9, wherein the human skin is foreskin.

13. The method according to claim 1, comprising allowing the skin area to rest for at least 3 weeks after irradiating the skin area.

14. The method according to claim 13, comprising allowing the skin area to rest for 3 to 4 weeks after irradiating the skin area.

15. The method according to claim 4, wherein the immunodeficient mouse is a SCID mouse.

16. The method according to claim 15, wherein the SCID mouse is BALB cA-nu/SCID or B-17/Icr-SCID.

17. The method according to claim 4, wherein irradiating the skin area comprises performing continuous irradiation.

18. The method according to claim 4, wherein irradiating the skin area comprises performing pulsed irradiation.

19. The method according to claim 4, wherein irradiating the skin area comprises irradiating five times per week.

20. The method according to claim 4, wherein the total dose of UV-B radiation is approximately 1.65 J/cm$^2$.

21. The method according to claim 4, wherein the total dose of UV-B radiation is approximately 2.85 J/cm$^2$.

22. An animal model which bears human photoaged skin and which is produced by the method according to claim 4.

23. The method according to claim 20, wherein the human skin is abdominal skin.

24. The method according to claim 21, wherein the human skin is foreskin.

25. The method according to claim 4, comprising allowing the skin area to rest for at least 3 weeks after irradiating the skin area.

26. The method according to claim 25, comprising allowing the skin area to rest for 3 to 4 weeks after irradiating the skin area.

* * * * *